(12) United States Patent
Jakoby et al.

(10) Patent No.: US 7,089,784 B2
(45) Date of Patent: Aug. 15, 2006

(54) DEVICE FOR EVALUATING THE SIGNAL FROM A VISCOSITY SENSOR

(75) Inventors: Bernhard Jakoby, Vienna (AT); Johannes Artzner, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 2 days.

(21) Appl. No.: 10/362,990

(22) PCT Filed: May 11, 2002

(86) PCT No.: PCT/DE02/01708

§ 371 (c)(1),
(2), (4) Date: Oct. 8, 2003

(87) PCT Pub. No.: WO03/004999

PCT Pub. Date: Jan. 16, 2003

(65) Prior Publication Data

US 2004/0045344 A1 Mar. 11, 2004

(30) Foreign Application Priority Data

Jun. 29, 2001 (DE) ............................. 101 31 429

(51) Int. Cl.
*G01N 11/00* (2006.01)

(52) U.S. Cl. .................................................... 73/54.02
(58) Field of Classification Search ............. 73/54.24, 73/54.41, 54.02, 53.05, 54.42, 579, 54.25
See application file for complete search history.

(56) References Cited

U.S. PATENT DOCUMENTS

| | | | | |
|---|---|---|---|---|
| 1,934,037 A | * | 11/1933 | Clark | 208/92 |
| 2,837,913 A | * | 6/1958 | Rich et al. | 73/54.01 |
| 2,849,398 A | * | 8/1958 | Molldy et al. | 508/357 |
| 4,142,401 A | * | 3/1979 | Wilson | 73/37.5 |
| 5,054,313 A | | 10/1991 | Fitzgerald et al. | |
| 5,271,267 A | | 12/1993 | Baumoel | |
| 5,698,773 A | * | 12/1997 | Blom et al. | 73/54.18 |
| 5,710,374 A | * | 1/1998 | Ross et al. | 73/54.24 |
| 6,250,147 B1 | | 6/2001 | Perten | |

FOREIGN PATENT DOCUMENTS

EP          0 884 578          12/1998

\* cited by examiner

*Primary Examiner*—Charles Garber
(74) *Attorney, Agent, or Firm*—Kenyon & Kenyon LLP

(57) ABSTRACT

A device is provided for evaluating the signal from a viscosity sensor having an amplifying circuit. The amplification of the amplifying circuit is controlled by a temperature signal from a temperature sensor.

2 Claims, 1 Drawing Sheet

DEVICE FOR EVALUATING THE SIGNAL FROM A VISCOSITY SENSOR

FIELD OF THE INVENTION

The present invention is directed to a device for evaluating the signal from a viscosity sensor.

BACKGROUND INFORMATION

In previously proposed devices, the signal from the viscosity sensor is amplified.

SUMMARY OF THE INVENTION

The device according to the present invention for evaluating the signal from a viscosity sensor, in contrast to the related art, has the advantage that partial compensation is made for the strong influence of temperature on the measurement variable viscosity. It is thus possible to greatly reduce the wide divergence in the range of values of the measurement signal caused by the influence of temperature on the viscosity, thereby permitting higher resolution in the evaluation of the measurement signal.

The use of an amplifier which an input for the signal from the viscosity sensor and an additional input for a signal from the temperature sensor is particularly simple. Amplification of the amplifier is controlled by the signal from a temperature sensor. It is advantageous if the viscosity sensor and the temperature sensor are situated in immediate proximity to one another in the measurement liquid; this ensures that the measurement values from the viscosity sensor and the temperature sensor are based on the same temperature. The design of the viscosity sensor as a microacoustic sensor is particularly simple.

DETAILED DESCRIPTION

Figure 1:
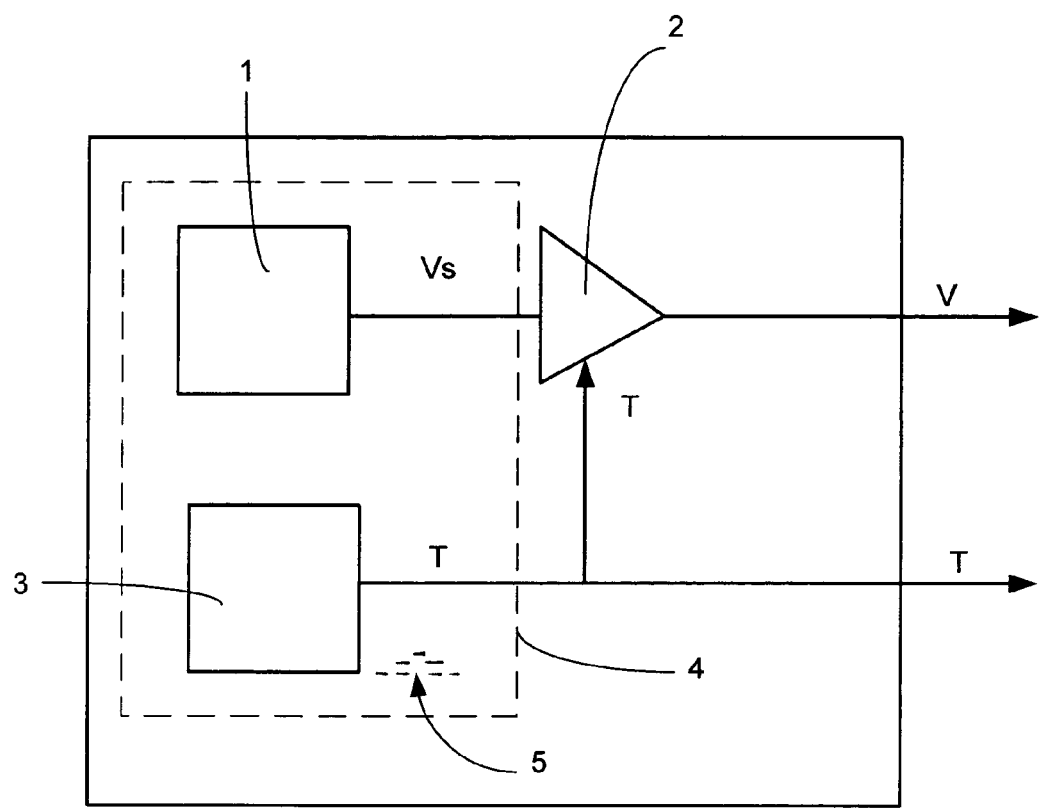
FIG. 1 shows one embodiment of the present invention.

FIG. 1 shows a block diagram of the device according to the present invention for evaluating the signal from a viscosity sensor. A viscosity sensor 1 schematically shown in FIG. 1, which produces a viscosity signal $V_S$ from the sensor. The signal $V_S$ is sent to an amplifying circuit 2, where the signal is amplified and the emitted as output signal V. The intensity of this output signal V is a measure of the viscosity of a measurement liquid. In addition, a temperature sensor 3 is provided which produces a temperature sensor signal T. Signal T from the temperature sensor is sent to an additional input of amplifier 2. Amplifier 2 is designed in such a way that the amplification of amplifier 2 is controlled depending on temperature signal T. In addition, temperature signal T is also externally emitted.

The device described in FIG. 1 suitable for determining the viscosity with partial compensation of the effect of temperature on the viscosity of the measurement medium. In particular, the determination of the oil quality in a motor vehicle engine is contemplated, in which the temperature of the engine oil varies from −20° C. to greater than +120° C. during the measurement operation. A viscosity sensor is provided in the oil pan, illustrated as element 4 in FIG. 1, for determining the viscosity. The measured viscosity of the engine oil 5 disposed within the oil pan 4 may be used for evaluating the quality, and may serve as a recommendation for an oil change. Using this measure, an unnecessary oil change may be prevented, or the maintenance interval of a motor vehicle engine may be set up for a correspondingly longer time.

A microacoustic sensor, for example, is used for the measurement of viscosity. In such microacoustic sensors an oscillating element is inserted into the oil, and the oscillation frequency of the oil or the damping of this oscillation is a measure of the viscosity. In the following description it is assumed that the oscillation frequency or damping is converted to an analog signal which represents the viscosity. (The frequency may be converted using a frequency-voltage transformer, for example.)

In such microacoustic sensors, a sensor signal VS from the viscosity sensor is proportional to density ρ or to viscosity η, according to formula 1:

$$V_S \propto (\rho\eta)^{1/2} \quad (1)$$

or alternatively, is proportional to a corresponding reciprocal value:

$$V_S \propto 1/(\rho\eta)^{1/2} \quad (2)$$

A typical sensor for engine oil has, for example, a sensor characteristic for viscosity as expressed by formula 2. In conjunction with dependence of the oil viscosity on temperature, this results in an approximately linear course of the viscosity signal VS from the sensor as a function of the temperature, according to the following formula:

$$VS \approx k1 + k2T \quad (3)$$

Constants k1 and k2 are constants which depend on the grade of oil. The dependence of the oil viscosity on temperature may thus be characterized by two constants. Sensor signal VS is fed into amplifier 2 and is amplified with amplification A:

$$V = A \cdot VS \quad (4)$$

According to the present invention, amplification A is provided with a temperature dependence so that emitted signal V is influenced by temperature as little as possible over the intended temperature range, and thus always represents a direct measure of the oil viscosity. For the dependence of viscosity on the temperature as represented in formula 3, an amplification is provided in the following form:

$$A \approx 1/(c1 + c2T) \quad (5)$$

Parameters C1 and C2 are again constants. Naturally, the constants are most favorably selected such that K1=C1 and K2=C2. This makes it possible for output signal V to be a fully temperature-dependent measure of the oil viscosity which is characterized by constants K1 and K2. Usually, constants C1 and C2 may be selected so that the parameters are very similar for the numerous engine oils, so that the temperature dependence of the viscosity measurement of engine oils may be significantly decreased. In this way, it is possible to prevent a wide divergence in the value range of V caused by the strong dependence of the oil viscosity on temperature. Consequently, subsequent digital processing results in significantly higher resolution in the viscosity measurement.

What is claimed is:

1. A device for evaluating a signal from a viscosity sensor sensing a medium, comprising:

an amplifying circuit for the signal from the viscosity sensor, wherein the amplifying circuit includes a predetermined temperature dependence for an amplification of the signal from the viscosity sensor as a function of the temperature of the medium, and wherein the signal from the viscosity sensor is dependent on a temperature T and constants (k1 and k2), and wherein the constants k1 and k2 depend on a grade of the medium, according to the following formula:

$$VS \approx k1 + k2T$$

wherein VS is the signal from the viscosity sensor.

2. A device for evaluating a signal from a viscosity sensor sensing a medium, comprising:

an amplifying circuit for the signal from the viscosity sensor, wherein the amplifying circuit includes a pre-determined temperature dependence for an amplification of the signal from the viscosity sensor as a function of the temperature of the medium, and wherein the amplification of the amplifying circuit is dependent on a temperature T and constants (c1 and c2), and wherein the constants c1 and c2 depend on a grade of the medium, according to the following formula:

$$A \approx 1/(c1 + c2T)$$

wherein A is the amplification of the amplifying circuit.

* * * * *